(12) United States Patent
Rausch et al.

(10) Patent No.: US 6,384,300 B1
(45) Date of Patent: May 7, 2002

(54) INVERTASE INHIBITOR

(75) Inventors: Thomas Rausch, Heidelberg; Silke Krausgrill, Frankfurt; Steffen Greiner, Offenbach, all of (DE)

(73) Assignee: University of Heidelberg, Heidelberg (DE)

( * ) Notice: Subject to any disclaimer, the term of this patent is extended or adjusted under 35 U.S.C. 154(b) by 0 days.

(21) Appl. No.: 09/230,670

(22) PCT Filed: Jul. 30, 1997

(86) PCT No.: PCT/EP97/04153

§ 371 Date: Apr. 5, 1999

§ 102(e) Date: Apr. 5, 1999

(87) PCT Pub. No.: WO98/04722

PCT Pub. Date: Feb. 5, 1998

(30) Foreign Application Priority Data

Jul. 30, 1996 (DE) .......................................... 196 30 738
Oct. 7, 1996 (DE) .......................................... 196 41 302

(51) Int. Cl.[7] .................. C12N 15/09; C12N 15/29; C12N 15/82; A01H 5/00
(52) U.S. Cl. .................. 800/284; 800/284; 800/278; 800/294; 800/295; 800/298; 800/317; 800/317.2; 800/317.4; 435/69.1; 435/69.2; 435/419; 435/468; 435/320.1; 435/69.7; 435/252.3; 435/430; 536/21.2; 536/23.6; 536/24.1
(58) Field of Search ................. 800/284, 295, 800/294, 298, 317, 317.2, 278, 317.4, 320.1; 435/69.1, 69.2, 69.7, 468, 419, 252.3, 430, 320.1; 536/23.2, 23.6, 24.1

(56) References Cited

U.S. PATENT DOCUMENTS 5,428,146 A * 6/1995 Logemann et al. ......... 536/24.1
5,917,127 A * 6/1999 Willmitzer et al. ......... 800/298

OTHER PUBLICATIONS

Bork, P. "Powers and Pitfalls in Sequence Analysis: The 70% Hurdle." 2000, Genome Research, vol. 10, pp. 398–400.*
Broun, P. et al., "Catalytic Plasticity of Fatty Acid Modification Enzymes Underlying Chemical Diversity of Plant Lipids." 1998, Science, vol. 282, pp. 1315–1317.*
Lazar, E. et al., "Transforming Growth Factor a: Mutation of Aspartic Acid 47 and Leucine 48 Results in Different Biological Activities." 1988, Molecular and Cellular Biology, vol. 8, pp. 1247–1252.*
Weil et al. Planta, vol. 193, pp. 438–445, 1994.*
Sander et al. FEBS letters, vol. 385, pp. 171–175, 1996.*
Russell, R. Phytochemistry, vol. 30, No. 3, pp. 543–546, 1994.*
Kossman et al. Progress in Biotechnol. 10, Proc. Int. Conf. 4/23–26, pp. 271–278, Apr. 1995.*
Smth et al. Nature, vol. 334, pp. 724–726, Aug. 1988.*
Chory et al. Plant Physiol. vol. 104, pp. 339–347, 1994.*
Sander et al. FEBS. vol. 385, pp. 171–175, Jun. 1996.*

* cited by examiner

Primary Examiner—Amy J. Nelson
Assistant Examiner—Medina A. Ibrahim
(74) Attorney, Agent, or Firm—Oscar A. Towler, III; Nexsen Pruet Jacobs & Pollard, LLC

(57) ABSTRACT

This invention relates to a nucleic acid that contains at least one nucleic acid sequence coding for a polypeptide, polypeptide being capable of reducing the enzymatic activity of an invertase; the polypeptide itself; and transgenic plants that contain this nucleic acid sequence. The invention further relates to methods of preparing such transgenic plants having reduced storage sucrose loss.

22 Claims, 14 Drawing Sheets

```
                10          20          30          40          50          60
                |           |           |           |           |           |
        ATGGGCGAGGAAAATGTCGTGCAGGTGATAACTCAGAACACACCGAATTATCAAGCTGCT
         M  G  E  E  N  V  V  Q  V  I  T  Q  N  T  P  N  Y  Q  A  A
                70          80          90         100         110         120
                |           |           |           |           |           |
          GGAAAGATGCTTGAAGAGAAAAGAAGGAATTTATTTTGGACTCCTTGTGCTGCATATTGT
           G  K  M  L  E  E  K  R  R  N  L  F  W  T  P  C  A  A  Y  C
               130         140         150         160         170         180
                |           |           |           |           |           |
         ATTGATCGCATCCTTGAAGACTTTGTGAAAATAAAATGGGTCAGAGAATGCATGGAAAAA
          I  D  R  I  L  E  D  F  V  K  I  K  W  V  R  E  C  M  E  K
               190         200         210         220         230         240
                |           |           |           |           |           |
         GCCCAAAAAATCACCAAGTTCATTTACAATAGTTTCTGGTTGTTAAGTCTCATGAAAAAA
          A  Q  K  I  T  K  F  I  Y  N  S  F  W  L  L  S  L  M  K  K
               250         260         270         280         290         300
                |           |           |           |           |           |
         GAATTTACAGCTGGACAGGAACTCTTGAAACCCTCTTTTACTCGATATTCTTCAACCTTC
          E  F  T  A  G  Q  E  L  L  K  P  S  F  T  R  Y  S  S  T  F
               310         320         330         340         350         360
                |           |           |           |           |           |
         GCTACTGTTCAGAGCTTGTTGGACCACAGAAATGGTCTTAAGAGGATGTTCCAGTCAAAT
          A  T  V  Q  S  L  L  D  H  R  N  G  L  K  R  M  F  Q  S  N
               370         380         390         400         410         420
                |           |           |           |           |           |
         AAATGGCTTTCGTCCCGGTATTCAAAGCTGGAAGATGGTAAAGAGGTGGAGAAAATTGTA
          K  W  L  S  S  R  Y  S  K  L  E  D  G  K  E  V  E  K  I  V
               430         440         450         460         470         480
                |           |           |           |           |           |
         CTAAATGCCACCTTCTGGAGGAAAATGCAGTATGTTAGGAAATCAGTGGACCCATTTTAG
          L  N  A  T  F  W  R  K  M  Q  Y  V  R  K  S  V  D  P  F  -
```

FIG. 1A

```
           490         500         510         520         530         540
            |           |           |           |           |           |
AAGTGCTTCAAAAAATCAATAGCAACGAAAGCCATTAATACCCTTCATTTACAACAATGT
  K   C   F   K   K   S   I   A   T   K   A   I   N   T   L   H   L   Q   Q   C 550         560         570         580         590         600
            |           |           |           |           |           |
ATACCAGGCAAAACTTGCTGTCAAAACCAATCATAATGACGACGGGGCAAATATCGGAAC
  I   P   G   K   T   C   C   Q   N   Q   S   -   -   R   R   G   K   Y   R   N 610         620         630         640         650         660
            |           |           |           |           |           |
ATTTTGGATATCATAGACAGCCACTGGAATTCATTATCTCATCATCCTCTCTATCTAGCA
  I   L   D   I   I   D   S   H   W   N   S   L   S   H   H   P   L   Y   L   A 670         680         690         700         710         720
            |           |           |           |           |           |
GCACACTTTCTGAATCCATCATACCGGTATCGTCCTGATTTTGTTCCGCATCCAGAGGTT
  A   H   F   L   N   P   S   Y   R   Y   R   P   D   E   V   P   H   P   E   V 730         740         750         760         770         780
            |           |           |           |           |           |
GTACGAGGACTGAATGCATGCATTGTGCGATTGGAGCCAGACAATGCAAGAAGAATTTCT
  V   R   G   L   N   A   C   I   V   R   L   E   P   D   N   A   R   R   I   S 790         800         810         820         830         840
            |           |           |           |           |           |
GCATCCATGCAAATATCAGATTTCAACTCTGCTTAAAGCTGATTTTGGAACAGATTTGGC
  A   S   M   Q   I   S   D   F   N   S   A   -   S   -   F   W   N   R   F   G 850         860         870         880         890         900
            |           |           |           |           |           |
ACTTAGCACCAGAACGGAGCTTAATCCTGCTGCTTGGTGGCAACAACATGGATAAATTGT
  T   -   H   Q   N   G   A   -   S   C   C   L   V   A   T   T   W   I   N   C 910         920         930         940         950         960
            |           |           |           |           |           |
TAGAGCTCCACCGATAGCTGGACGAATACTAGCAGACTGTCACTTGGTGTGAGCACAATT
  S   S   T   D   S   W   T   N   S   R   L   S   L   G   V   S   T   I
```

FIG. 1B

```
         970       980       990      1000      1010      1020
          |         |         |         |         |         |
GGAGTTATATCATCAGATCCACAGTCAGAGGCACAACCGTGTAGCACAGAAAGATTAAAC
  G  V  I  S  S  D  P  Q  S  E  A  Q  P  C  S  T  E  R  L  N
        1030      1040      1050      1060      1070      1080
          |         |         |         |         |         |
GATGTCACATACGTCCACTATAACCTGAGACTTAGGGATCGTCAGATAAGGAAAATGCCT
  D  V  T  Y  V  H  Y  N  L  R  L  D  R  Q  I  R  K  M  P
        1090      1100      1110      1120      1130      1140
          |         |         |         |         |         |
ATCATCCAATTTTCCTCGATAGTGTTCTGCAAGAAATTTGCTGTATGATTGGATTGTAGA
  I  I  Q  F  S  S  I  V  F  C  K  K  F  A  V  -  L  D  C  R
        1150      1160      1170      1180      1190      1200
          |         |         |         |         |         |
GTCAGAGAAACCAGTTTTGCAAGACGATGAGGAAATGCTTTATAGTGAAATGGAACTGGT
  V  R  E  T  S  F  A  R  R  -  G  N  A  L  -  -  N  G  T  G
        1210      1220      1230      1240      1250      1260
          |         |         |         |         |         |
GAGTATGAGAATGATTTCATGGACCATGATGNTGGAAATNCANACTTAAGGAAGGGATCA
  E  Y  E  N  D  F  M  D  H  D  X  G  N  X  X  L  R  K  G  S
        1270      1280      1290      1300      1310      1320
          |         |         |         |         |         |
TTGGAGATGGTAACTTTAGCTGGTGAAGCAGAACCCCTAGAAGTTAATCCTGACAATACT
  L  E  M  V  T  L  A  G  E  A  E  P  L  E  V  N  P  D  N  T
        1330      1340      1350      1360      1370      1380
          |         |         |         |         |         |
GGTACAGCTACAGATGATGATTCTGATCTCAATTTTCTTGATAATGAGTTGAGTGATTAG
  G  T  A  T  D  D  D  S  D  L  N  F  L  D  N  E  L  S  D  -
        1390      1400      1410      1420      1430      1440
          |         |         |         |         |         |
TGCCTTGAACCAGAACCCAAATGCACAGCAGTTAACATGTTTGGTAACCACTCAACTACT
  C  L  E  P  E  P  K  C  T  A  V  N  M  F  G  N  H  S  T  T
```

FIG. 1c

```
        1450      1460      1470      1480      1490      1500
         |         |         |         |         |         |
GGCAATGTATTCTATTATCGCAAGTCCTTTAGCTATCTCTCCCAATCACTTTCTTGGCAA
  G   N   V   F   Y   Y   R   K   S   F   S   Y   L   S   Q   S   L   S   W   Q
        1510      1520      1530      1540      1550      1560
         |         |         |         |         |         |
AATGTGCACTGCCAGTTGGGCGAGTGGGGACGGGAAAGGGGGGAAAAGTCGGAAAGAGCC
  N   V   H   C   Q   L   G   E   W   G   R   E   R   G   E   K   S   E   R   A
        1570      1580      1590      1600      1610      1620
         |         |         |         |         |         |
TGTGTAGAAGTTAGAGATCAGCATTACAGGAGGGCACTGGAGTGTACATGTCAAAGTACT
  C   V   E   V   R   D   Q   H   Y   R   R   A   L   E   C   T   C   Q   S   T
        1630      1640      1650      1660      1670      1680
         |         |         |         |         |         |
TCGTTTCTTAACCTCTCACTGTTCATGTTTAGTCATTGTTTGCTCTTATTCAGTTTTCCT
  S   F   L   N   L   S   L   F   M   F   S   H   C   L   L   F   S   F   P
        1690      1700
         |         |
TCAAAAAAAAAAAAAAAAAAAA
  S   K   K   K   K   K
```

Fig. 1D

P = SPECIFIC PROMOTER OF THE TARGET PLANT

S = SIGNAL SEQUENCE

ORF = OPEN READING FRAME OF THE INHIBITOR cDNA

VT = VACUOLAR TARGETING SEQUENCE

```
         10        20        30        40        50        60
         |         |         |         |         |         |
AGAAAATCTAACTTTGGTTCTCTCTCTCTTGTCTTTTCCAACTTCAAAAATGAAGAATTT
  E  N  L  T  L  V  L  S  L  L  S  F  P  T  S  K  M  K  N  L
         70        80        90       100       110       120
         |         |         |         |         |         |
GATTTTCCTAACGATGTTTCTGACTATATTACTACAAACAAACGCCAATAATCTAGTAGA
  I  F  L  T  M  F  L  T  I  L  L  Q  T  N  A  N  N  L  V  E
        130       140       150       160       170       180
         |         |         |         |         |         |
AACTACATGCAAAAACACACCAAATTACCAACTTTGTCTGAAAACTCTGCTTTCGGACAA
  T  T  C  K  N  T  P  N  Y  Q  L  C  L  K  T  L  L  S  D  K
        190       200       210       220       230       240
         |         |         |         |         |         |
ACGAAGTGCAACAGGGGATATCACAACGTTGGCACTAATTATGGTCGATGCAATAAAAGC
  R  S  A  T  G  D  I  T  T  L  A  L  I  M  V  D  A  I  K  A
        250       260       270       280       290       300
         |         |         |         |         |         |
TAAAGCTAATCAGGCTGCAGTGACAATTTCGAAACTCCGGCATTCGAATCCCCCTGCAGC
  K  A  N  Q  A  A  V  T  I  S  K  L  R  H  S  N  P  P  A  A
        310       320       330       340       350       360
         |         |         |         |         |         |
TTGGAAAGGTCCTTTGAAAAACTGTGCCTTTTCATATAAGGTAATTTTAACAGCAAGTTT
  W  K  G  P  L  K  N  C  A  F  S  Y  K  V  I  L  T  A  S  L
        370       380       390       400       410       420
         |         |         |         |         |         |
GCCTGAAGCAATTGAAGCATTGACAAAAGGAGATCCAAAATTTGCTGAAGATGGAATGGT
  P  E  A  I  E  A  L  T  K  G  D  P  K  F  A  E  D  G  M  V
        430       440       450       460       470       480
         |         |         |         |         |         |
AGGTTCATCTGGAGATGCACAAGAATGTGAGGAGTATTTCAAGGGTAGTAAATCACCATT
  G  S  S  G  D  A  Q  E  C  E  E  Y  F  K  G  S  K  S  P  F
        490       500       510       520       530       540
         |         |         |         |         |         |
TTCTGCATTAAATATAGCAGTTCATGAACTTTCTGATGTTGGGAGAGCTATTGTCAGAAA
  S  A  L  N  I  A  V  H  E  L  S  D  V  G  R  A  I  V  R  N
        550       560       570       580       590       600
         |         |         |         |         |         |
TTTATTGTGATATATATGCACTACTCTTATACAAGTGTAACAATATTATCGATCAGAAAT
  L  L  -
        610       620       630       640
         |         |         |         |
TTATTATGATGTGCCTGTGTATTCACACGTGAAAAAAAAAAAAAAAAAA
```

Fig. 3

```
         10        20        30        40        50        60
         |         |         |         |         |         |
AAGAACACACCGAATTACCATTTGTGTGTGAAAACTTTGTCTTTAGACAAAAGAAGTGAA
  K  N  T  P  N  Y  H  L  C  V  K  T  L  S  L  D  K  R  S  E
         70        80        90       100       110       120
         |         |         |         |         |         |
AAAGCAGGAGATATTACAACATTAGCATTAATTATGGTTGATGCTATTAAATCTAAAGCT
  K  A  G  D  I  T  T  L  A  L  I  M  V  D  A  I  K  S  K  A
                                     ─
         130       140       150       160       170       180
         |         |         |         |         |         |
AATCAAGCTGCTAATACTATTTCAAAACTTAGGCATTCTAATCCTCCTCAAGCTTGGAAA
  N  Q  A  A  N  T  I  S  K  L  R  H  S  N  P  P  Q  A  W  K
         190       200       210       220       230       240
         |         |         |         |         |         |
GATCCTTTGAAGAATTGTGCCTTTTCGTATAAGGTAATTTTAACAGCAAGTATGCCAGAA
  D  P  L  K  N  C  A  F  S  Y  K  V  I  L  T  A  S  M  P  E
         250       260       270       280       290       300
         |         |         |         |         |         |
GCAATAGAAGCATTAACAAAAGGTGATCCAAAATTTGCAGAAGATGGAATGGTCGGATCA
  A  I  E  A  L  T  K  G  D  P  K  F  A  E  D  G  M  V  G  S
                                                       ─

TCAGGTG
  S  G
```

FIG. 12

```
tomato-INHI   --------KNTPNYHLCVKTLSLDKRSEKAGDITTLALIMVDAIKSKANQ  42
tomato-INHI   --------KNTPNYHLCVKTLSLDKRSEKAGDITTLALIMVDAIKSKANQ  42
tobacco-INH   NNLVETTCKNTPNYQLCVKTLLSDKRSA-TGDITTLALIMVDAIKAKANQ  49 tomato-INHI   AANTISKLRHSNPPQAWKDPLKNCAFSYKVILTASMPEAIEALTKGDPKF  92
tomato-INHI   AANTISKLRHSNPPQAWKDPLKNCAFSYKVILTASMPEAIEALTKGDPKF  92
tobacco-INH   AANTISKLRHSNPPQAWKDPLKNCAFSYKVILTASMPEAIEALTKGDPKF  99
              ** ********** *** ***************** **************
                              .  .                .

tomato-INHI   AEDGMVGSSG----------------------------------------  102
tomato-INHI   AEDGMVGSSG----------------------------------------  102
tobacco-INH   AEDGMVGSSGDAQECEEYFKGSKSPFSALNIAVHELSDVGRAIVRNLL   147
              **********
```

Fig. 13

```
                                    40         50         60
                                    |          |          |
CGGCACGAGAACAAAACCAAACACCTTTCCTTTGGCCTCTCCTCCTTTTATCTTTTATAT
  R  H  E  N  K  T  K  H  L  S  F  G  L  S  S  F  Y  L  L  Y
       70         80         90        100        110        120
       |          |          |          |          |          |
CAATCCTCATCTTCAATAACACCACTCTCAAAACAAATGAGAAACTTATTCCCCATATTT
  Q  S  S  S  I  T  P  L  S  K  Q  M  R  N  L  F  P  I  F
      130        140        150        160        170        180
       |          |          |          |          |          |
ATGTTAATCACCAATCTAGCATTCAACGACAACAACAACAGTAATAATATCATCAACACG
  M  L  I  T  N  L  A  F  N  D  N  N  N  S  N  N  I  I  N  T
      190        200        210        220        230        240
       |          |          |          |          |          |
ACCTGCAGAGCCACCACAAACTACCCCTTGTGCCTCACCACCCTCCACTCTGATCCCCGT
  T  C  R  A  T  T  N  Y  P  L  C  L  T  T  L  H  S  D  P  R
      250        260        270        280        290        300
       |          |          |          |          |          |
ACCTCCGAGGCCGAGGGGGCGGACCTCACCACCCTCGGCCTCGTCATGGTAGATGCGGTA
  T  S  E  A  E  G  A  D  L  T  T  L  G  L  V  M  V  D  A  V
      310        320        330        340        350        360
       |          |          |          |          |          |
AAATTAAAGTCCATCGAAATAATGAAAAGTATAAAAAAACTCGAAAAATCGAACCCCGAG
  K  L  K  S  I  E  I  M  K  S  I  K  K  L  E  K  S  N  P  E
      370        380        390        400        410        420
       |          |          |          |          |          |
TTGAGACTACCTCTTAGCCAATGTTACATAGTGTATTATGCTGTTCTACATGCTGATGTA
  L  R  L  P  L  S  Q  C  Y  I  V  Y  Y  A  V  L  H  A  D  V
      430        440        450        460        470        480
       |          |          |          |          |          |
ACTGTTGCTGTTGAAGCTTTAAAAAGAGGAGTCCCTAAATTTGCTGAAAATGGAATGGTT
  T  V  A  V  E  A  L  K  R  G  V  P  K  F  A  E  N  G  M  V
```

FIG.14A

```
           490       500       510       520       530       540
            |         |         |         |         |         |
         GATGTTGCTGTAGAAGCAGAAACTTGTGAGTTTAGTTTTAAGTATAATGGATTGGTTTCT
           D  V  A  V  E  A  E  T  C  E  F  S  F  K  Y  N  G  L  V  S
           550       560       570       580       590       600
            |         |         |         |         |         |
         CCAGTTTCTGATATGAATAAGGAGATTATTGAACTGTCTTCTGTGGCTAAATCTATTATT
           P  V  S  D  M  N  K  E  I  I  E  L  S  S  V  A  K  S  I  I
           610       620       630       640       650       660
            |         |         |         |         |         |
         AGAATGCTATTATGAGGAAATTAAAGAACCAAAGATACAAGGTTCTGGTTATGTTAGTTT
           R  M  L  L
                     670       680       690       700       710       720
                      |         |         |         |         |         |
         ATTAGTGCTGTAATAGGATTTTTATATTCCTGTGTTTTTTTGCTTTTTTTATTTCATTT
                     730       740       750       760       770       780
                      |         |         |         |         |         |
         GGGTGCTTGTGTGTATATGTGAAAATGAGTGTGAATTATGTCAAACATAAACATAGATTA
                     790       800       810
                      |         |         |
         GAAATTACTCCTGAAAAAAAAAAAAAAAAAA
```

FIG. 14B

INVERTASE INHIBITOR

This invention relates to a nucleic acid that contains at least one nucleic acid sequence coding for a polypeptide, said polypeptide being capable of reducing the enzymatic activity of an invertase, the polypeptide itself, as well as transgenic plants that contain this nucleic acid sequence. The invention further relates to methods of preparing such transgenic plants with reduced storage sucrose loss.

BACKGROUND OF THE INVENTION

During the storage of sugar beets (*Beta vulgaris*), in the period between harvest and processing, respiration or sucrose metabolism leads to a sucrose loss of roughly 0.02% per day. This loss is further accompanied by a significant diminution of quality as a consequence of the increase of reducing sugars, in particular fructose and glucose (Burba, M. (1976), "Respiration and Sucrose Metabolism of Sugar Beets in Storage," *Zeitschrift für die Zuckerindustrie* 26:647–658). The first metabolic step in the breakdown of sucrose during the storage of beets is enzymatic hydrolysis by a vacuolar invertase. This enzyme is synthesized de novo in the beet tissue after injury (Milling, R. J., Leigh, R. A., and Hall, J. L. (1993), "Synthesis of a Vacuolar Acid Invertase in Washed Discs of Storage Root Tissue of Red Beet (*Beta vulgaris* L.), *J. Exp. Bot.* 44:1687–1694). Because the bulk of beet sucrose is localized in the vacuoles of the cell, the (injury-)induced vacuolar invertase plays a central role in storage sucrose loss.

At present there is no satisfactory solution to the problem of storage sucrose losses (Burba, 1976). The most important practices in the prior art consist in maintaining low temperatures (below 12° C.) and a well-defined atmospheric humidity (between 90 and 96%). All practices used up to now to reduce the storage losses are, however, unsatisfactory.

Conversion of sucrose to the hexoses glucose and fructose in storage, and thus loss of sucrose, also occurs during the "cold sweetening" of potatoes. As a result of cold processing, a vacuolar invertase is induced in the potato tubers and determines the ratio of sucrose to hexoses (Zrenner, R., Schüler, K., and Sonnewald, U. (1996), "Soluble Acid Invertase Determines the Hexose-to-Sucrose Ratio in Cold-Stored Potato Tubers," *Planta* 198:246–252). The formation of hexoses as a result of cold sweetening leads to diminutions of quality in the making of, for example, French-fried potatoes.

Tomato fruits (*Lycopersicon esculentum* Mill.) exhibit a high water content. This is due in part to the osmotically active endogenous sugars (sucrose and hexoses). Lowering the total sugar content by means of inhibiting the invertase-mediated hydrolysis of sucrose leads to smaller fruits with lower water content (Klann, E. M., Hall, B., and Bennett, A. B. (1996), "Antisense Acid Invertase (TIV1) Gene Alters Soluble Sugar Composition and Size in Transgenic Tomato Fruit," *Plant Physiology* 112:1321–1330). Reducing the water content of the tomato fruits leads to a saving in energy costs for the production of fruit concentrates (e.g., ketchup). Because the reduction of vacuolar invertase activity via invertase antisense expression is incomplete because of the occurrence of a variety of isoforms, the transgenic introduction of an invertase inhibitor might result in great advantages, in particular if said invertase inhibitor has an equal inhibiting action on these various isoforms.

SUMMARY OF THE INVENTION

It is therefore an object of the invention to create a new system that causes essentially no sucrose storage-related losses in plants.

This object is achieved by virtue of the subject matters of the invention characterized in the Claims.

DETAILED DESCRIPTION

A first subject matter of the invention relates to a nucleic acid that contains at least one nucleic acid sequence coding for a polypeptide, which polypeptide is capable of reducing or lowering the enzymatic activity of an invertase.

The terms "nucleic acid" and "nucleic acid sequence" denote natural or semisynthetic or synthetic or modified nucleic acid molecules from deoxyribonucleotides and/or ribonucleotides and/or modified nucleotides.

The term "polypeptide" denotes naturally occurring polypeptides and recombinant polypeptides. Recombinant polypeptides denote a construct prepared by molecular-biological techniques, based on the natural DNA of the original genome or the natural DNA modified with a foreign DNA sequence, which construct can be recombined, for example with plasmids, and replicated and expressed in a suitable host system.

The expression "a polypeptide capable of reducing the enzymatic activity of an invertase" denotes a polypeptide that, in the process of binding to an invertase, reduces the enzymatic activity of said invertase, complete inhibition being possible if there is a sufficient quantity of the inhibitor protein. A roughly 90% inhibition of the vacuolar invertase is preferably to be achieved by means of the inhibitor expression in the transgenic plant.

In an embodiment of the invention, the invertase in a plant cell is vacuolarly localized. In another embodiment, the invertase is localized in the cell wall. In a further embodiment, the invertase is localized in the cytosol. The invertase is preferably derived from sugar beet, potato or tomato.

In a preferred embodiment of the invention, the nucleic acid comprises the nucleic acid sequences shown in FIGS. 1(*a*)–1(*d*) (SEQ ID No. 1), 3 (SEQ ID No. 2), 12 (SEQ ID No. 3) and 14(*a*)–(*b*) (SEQ ID No. 4) or segments or fragments thereof as well as nucleic acid sequences that can hybridize with the complementary sequences of the nucleic acid sequences shown in FIGS. 1(*a*–*d*), 3, 12 or 14(*a*)–(*b*) or segments or fragments thereof.

In another embodiment, the nucleic acid according to the invention contains a further nucleic acid sequence coding for a targeting sequence. The term "targeting sequence" denotes an amino acid sequence that mediates cellular targeting into a well-defined cellular compartment, for example targeting into the vacuoles.

In a preferred embodiment of the invention, the targeting sequence comprises the vacuolar targeting sequence of barley lectin having the following amino acid sequence:

SEQ ID NO: 9 LEGVFAEIAASNSTLVAE

In another embodiment, the nucleic acid according to the invention contains a further nucleic acid sequence coding for a signal peptide. The term "signal peptide" denotes a hydrophobic amino acid sequence that is recognized by the signal recognition particle (SRP). The SRP mediates the synthesis of the entire polypeptide on the rough endoplasmic reticulum (ER), with the consequence that the resulting polypeptide is released into the ER lumen.

In a further embodiment, the nucleic acid according to the invention contains a nucleic acid sequence coding for an ER retention sequence.

In a preferred embodiment, the signal peptide is derived from an invertase, preferably from cell-wall invertase from tobacco.

In another embodiment of the invention, the nucleic acid contains a further nucleic acid sequence that comprises a promoter suitable for expression in plants. This promoter or promoter sequence is preferably derived from the same plant as the invertase. In an especially preferred embodiment of the invention, the promoter is a promoter specific to potato or sugar beet.

In summary, the nucleic acid according to the invention can comprise the above-defined nucleic acid sequence coding the polypeptide and, if appropriate, the above-defined nucleic acid sequence coding a targeting sequence and/or the above-defined promoter, where all nucleic acid sequences coding an amino acid sequence are preferably arranged in the reading frame and can be degenerated in accordance with the genetic code.

A further subject matter of the invention is a vector that contains the above-defined nucleic acid according to the invention for the expression of the recombinant polypeptide in prokaryotic or eukaryotic host cells. The vector according to the invention can preferably contain suitable regulatory elements such as promoters, enhancers, termination sequences. The vector according to the invention can be, for example, an expression vector or a vector for the preferably stable integration of the nucleic acid according to the invention in to the genetic material of a host cell. A suitable expression system comprises, for example, the Ti plasmid or a binary plasmid system in *Agrobacterium tumefaciens* as vector for the stable integration of the nucleic acid according to the invention into the genetic material of a plant. Further, the nucleic acid according to the invention can, for example, also be inserted into the genetic material of a plant by means of the Ri plasmid of *Agrobacterium rhizogenes,* by means of direct gene transfer via polyethylene glycol, by means of electroporation, or by means of particle bombardment.

A further subject matter of the invention is a host cell that contains the nucleic acid according to the invention or the vector according to the invention. Suitable host cells are, for example, prokaryotes such as *E. coli* or eukaryotic host cells such as *Saccharomyces cerevisiae, Schizosaccharomyces pombe, Hansenula polymorpha, Pichia pastoris* and baculovirus-infected insect cells.

A further subject matter of the invention is the polypeptide itself that is coded by the above-defined nucleic acid sequence, where the nucleic acid sequence can be degenerated in accordance with the genetic code. The polypeptide according to the invention contains at least one amino acid sequence segment capable of reducing the enzymatic activity of an invertase. In an especially preferred embodiment, the polypeptide comprises the amino acid sequences shown in FIGS. 1(a)–1(d) (SEQ ID No. 5), 3 (SEQ ID No. 6), 12 (SEQ ID No. 7) and 14(a)–14(b) (SEQ ID No. 8) or segments or fragments thereof. The term "polypeptide" further comprises, for example, iso forms from the same plant as well as homologous inhibitor sequences of other plant species, the homology at the protein level preferably being >70%.

In a embodiment of the invention, the polypeptide further contains an amino acid sequence arranged at the C-terminus of the polypeptide, which amino acid sequence comprises an above-defined targeting sequence and/or an ER retention sequence, for example "KDEL," and/or an amino acid sequence arranged at the N-terminus of the polypeptide, which amino acid sequence comprises an above-defined signal peptide.

The nucleic acid sequence according to the invention, the vector according to the invention, and the polypeptide according to the invention can be prepared by means of prior art methods.

A further subject matter of the invention is a transgenic plant that contains at least the above-defined nucleic acid according to the invention.

The term "transgenic plant" or "plant" comprises the entire plant as such as well as its parts, such as root, stem, leaf, organ-specific tissue or cells, its reproductive material, in particular seeds, and its embryos. This term further comprises starchy tubers and starchy roots, for example potato, sweet potato and cassava, and sugar plants, for example sugar cane and sugar beet, as well as tomato and maize.

In a preferred embodiment of the invention, the wild type of the transgenic plant is a sugar beet, a tomato or a potato.

A further subject matter of the invention relates to a method of preparing the transgenic plant according to the invention, wherein a plant cell is transformed by means of stable integration of the above-defined nucleic acid into the genetic material and the transformed plant cell is regenerated to the transgenic plant.

Methods of preparing transgenic plants are known in the prior art.

A further subject matter of the invention relates to the use of the above-defined nucleic acid for the preparation of a transgenic plant having reduced storage sucrose loss.

It can be stated according to the invention that the reduction in storage sucrose losses by means of the expression of the above-defined polypeptide as "invertase inhibitor protein" in transgenic plants represents, surprisingly, a highly specific, environmentally safe method for improving the quality of, for example, sugar beets or potato tubers. For sugar beet, a reduction in required production capacity is made possible by means of the boost in the efficiency of sugar recovery for a given level of productiveness. In the case of potato, the product quality of potatoes, in particular for the making of French-fried potatoes, is enhanced by means of the reduction in cold-induced hexose formation. In the case of tomato, the water content of the tomato fruit is lowered by means of the reduction of osmotically active hexoses.

By means of the combination of the nucleic acid sequence encoding the invertase inhibitor with a nucleic acid sequence encoding a suitable targeting sequence, correct vacuolar targeting of the expressed invertase inhibitors into the vacuoles can, for example, be achieved and thus the expression of the invertase inhibitor can be restricted in space. Further, the expression of the invertase inhibitor can be restricted in time by means of the use of promoters specific to, for example, beet or tuber.

BRIEF DESCRIPTION OF THE FIGURES

The Figures show the following:

FIGS. 1(a)–1(d) shows the cDNA from *Nicotiana tabacum* encoding the invertase inhibitor, having a length of 1701 bp, the open reading frame (ORF) comprising 477 bp with starting nucleotide 1. The invertase inhibitor coded by this nucleic acid sequence exhibits 159 amino acids with a calculated molecular weight $M_r$ of 18915 and a calculated isoelectric point of 10.13.

FIG. 3 shows a further cDNA coding for an invertase inhibitor localized in the cell wall of tobacco cells, having a length of 631 bp (exclusive of poly(A)). The signal sequence used for secretion into the cell wall is marked italicized. The site of cleavage, which is identical to the partially sequenced N-terminus of the mature protein, is marked by means of an arrow.

FIG. 12 shows the sequence of a partial cDNA of the tomato invertase inhibitor, which was amplified from tomato flower cDNA by RT-PCR.

FIG. 13 shows a comparison of two (identical) partial tomato invertase inhibitor clones with the tobacco invertase inhibitor (see FIG. 3).

FIGS. 14(a)–(b) shows the cDNA sequence of a cytosolic homolog of the invertase inhibitor clone of FIG. 3. The protein encoded by this clone is capable of inhibiting cytosolic invertases.

The invention is explained in more detail by means of the example that follows.

EXAMPLE

All methods used in the following example for the preparation of the required gene constructs correspond to standard methods for work in molecular biology (Ausubel, F., Brent, R., Kingston, R. E., Moore, D. D., Seidmann, J. G., Smith, J. A., and Struhl, K. (1987–1996), *Current Protocols in Molecular Biology*, Greene Publishing). The procedure can be subdivided into essentially the following steps:

(1) The inhibitor protein is purified to homogeneity by selective salt elution of the cell-wall protein, twofold ion-exchange chromatography, and subsequent SDS polyacrylamide gel electrophoresis.

(2) The homogeneous inhibitor protein is subjected to tryptic digestion, and the resulting peptides of the inhibitor protein are sequenced by Edman degradation.

(3) On the basis of the peptide sequences obtained, degenerate primers are synthesized; with their help, DNA fragments of the inhibitor cDNA are amplified from the overall cDNA by PCR.

(4) A cDNA library is prepared from tobacco cell cultures (in an expression vector: Stratagene ZAP Express®).

(5) The resulting partial sequences of inhibitor cDNA (see step 2) are used for screening the cDNA library.

(6) The obtained full-length clone, after expression in *E. coli* (cloning into the Qiagen pQE vector), is confirmed as to its function (invertase inhibition).

Figure 4:
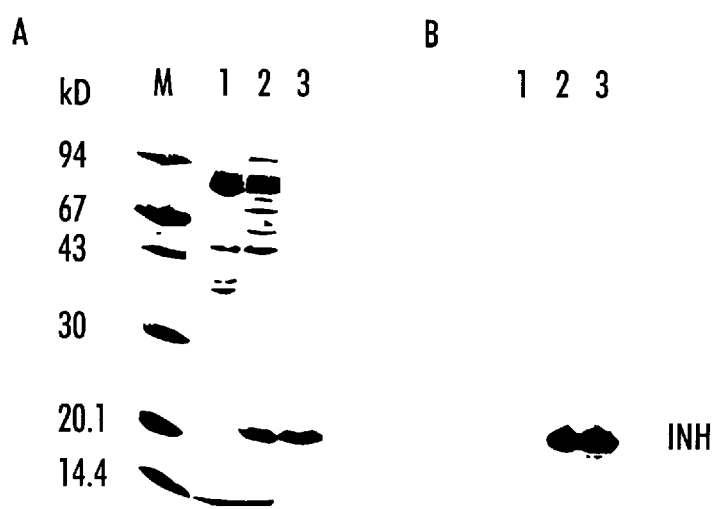
FIG. 4 shows the expression of the recombinant tobacco invertase inhibitor in *E. coli*. The cDNA shown in FIG. 3 was cloned into the pQE vector (Qiagen, Hilden, Germany). The recombinant protein was expressed as a His-tagged fusion protein. 4A: M, molecular-weight marker; 1: bacteria, noninduced; 2: bacteria induced with IPTG; 3: recombinant tobacco invertase inhibitor purified by affinity chromatography (Ni-NTA). 4B: Western Blot analysis of fractions 1–3 from A with a polyclonal antiserum directed against the inhibitor.

(7) The segment of the cDNA clone coding for the inhibitor protein (FIG. 1) is amplified by PCR. Primers having restriction cleavage-sites that permit subsequent ligation with the signal sequence and the targeting sequence are used for this purpose. The signal sequence is ligated to the 5' end, while the targeting sequence for the vacuoles is ligated to the 3' end. Recovery of signal sequence: The signal sequence is amplified from the cDNA of the tobacco cell-wall invertase (Greiner, S., Weil, M., Krausgrill, S., and Rausch, T. (1995), *Plant Physiology* 108:825–826) by PCR (region $Met^1$-$Val^{23}$). Primers having restriction cleavage-sites that permit subsequent ligation to the inhibitor cDNA are used for this purpose. Recovery of targeting sequence: The targeting sequence is amplified from the cDNA for barley lectin (Bednarek, S. Y., and Taikhel, N. V. (1991), *Plant Cell* 3:1195–1206). Again, primers having restriction cleavage-sites that permit subsequent ligation to the inhibitor cDNA are used for this purpose. For the sense cloning of the nucleic acid shown in FIG. 3 (SEQ ID No. 2), the entire nucleic acid is excised from the pBK-CMV vector (which is generated by in vivo excision from the Stratagene ZAP Express phages) with the help of the restriction endonucleases BamHI and XbaI. The DNA fragment obtained is now ligated into a BamHI/XbaI cleaved binary transformation vector and then transformed into bacteria. For the antisense cloning of the nucleic acid shown in FIG. 3 (SEQ ID No. 2), the restriction endonucleases BamHI and KpnI are employed. Otherwise, the procedure is the same as in the sense cloning. An analogous procedure is used for the sense and antisense cloning of the nucleic acid from FIGS. 14(a)–14(b) (SEQ ID No. 4). The constructs thus obtained are used for *Agrobacterium tumefaciens*-mediated gene transfer into plants (sugar beet, potato and tomato in the example). The insertion of the vacuolar targeting sequence for the nucleic acids from FIGS. 3 and 4 is carried out as described for the nucleic acid from FIGS. 1(a)–1(d).

(8) The 5' end of the gene construct cited in (7) is ligated to a beet-specific promoter, and the resulting construct is cloned into a binary expression vector.

Figure 2:
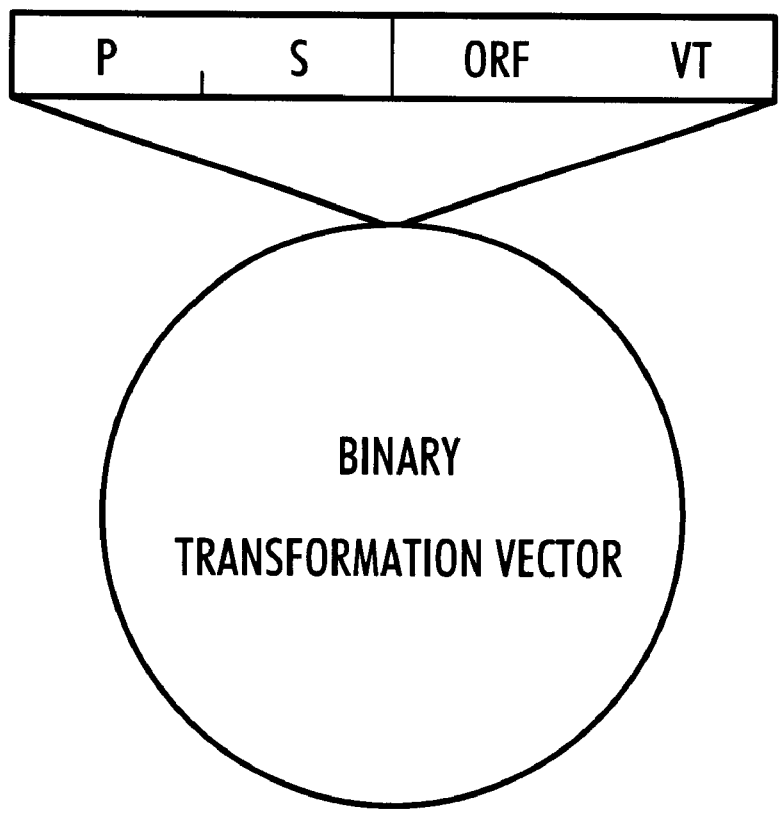
FIG. 2 shows the schematic preparation of the inhibitor construct of a preferred embodiment of the invention for the transformation of plants.

(9) The target plant is transformed by a suitable prior art transformation method. The structure of the gene construct used for the transformation is shown in FIG. 2.

Figure 5:
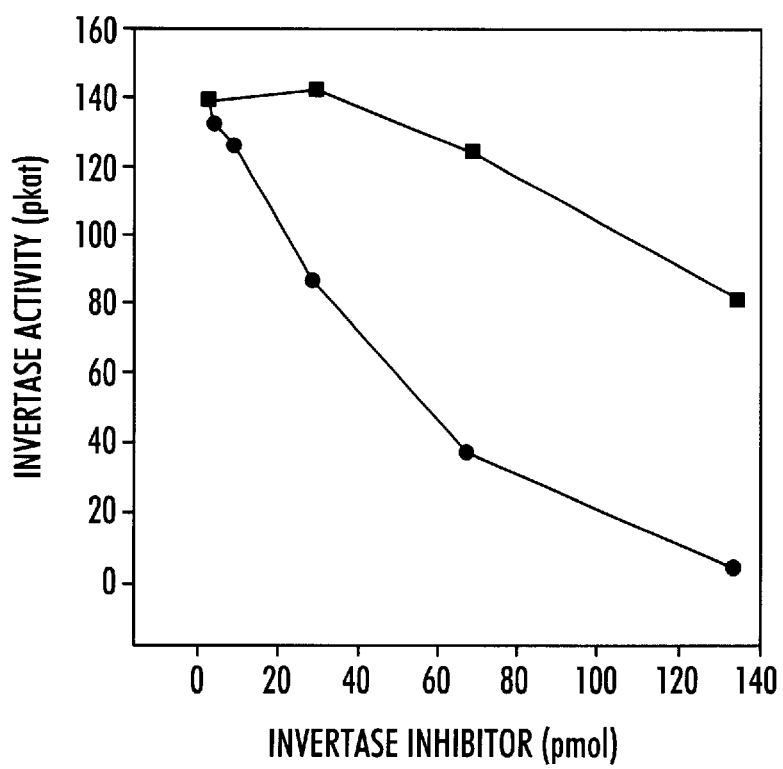
FIG. 5 shows dose-dependent inhibition of the cell-wall invertase from tobacco by means of the recombinant inhibitor protein. The circles show inhibition after preincubation of both proteins without sucrose; the squares show inhibition without preincubation.

An antiserum against the invertase inhibitor expressed in tobacco cells was developed for screening a cDNA library. A homologous cDNA probe was also obtained by PCR reactions with oligonucleotides derived from partial amino acid sequences. Furthermore, a screening with oligonucleotides was performed. The clone in FIGS. 1(a)–1(d) was isolated with the oligonucleotide screening. A 300 bp fragment was amplified by RT-PCR and then employed as a probe for screening the cDNA library. The clone in FIG. 3 was isolated in this way. The latter was expressed in E. coli as a His-tagged fusion protein (FIG. 4). The recombinant inhibitor protein inhibits the cell-wall invertase from tobacco, a partial protection of the substrate being observed for this invertase iso form (FIG. 5), said protection not occurring, however, with other vacuolar invertases or invertases localized in the cell wall (see below). What is more, a homolog to the inhibitor clone shown in FIG. 3, localized in the cytosol, was isolated (FIGS. 14(a)–14(b)). The protein coded by this clone can act as an inhibitor for cytosolic invertases.

Figure 6:
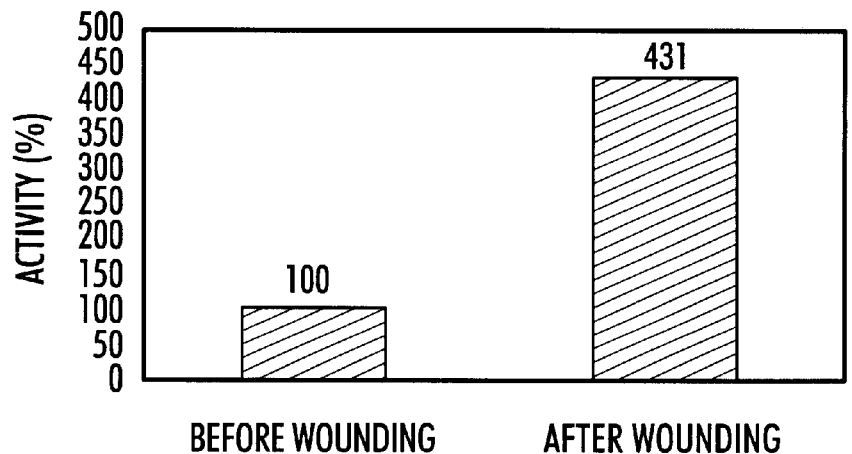
FIG. 6 shows the induction of acid invertase activity in sugar beets after injury.
Figure 7:
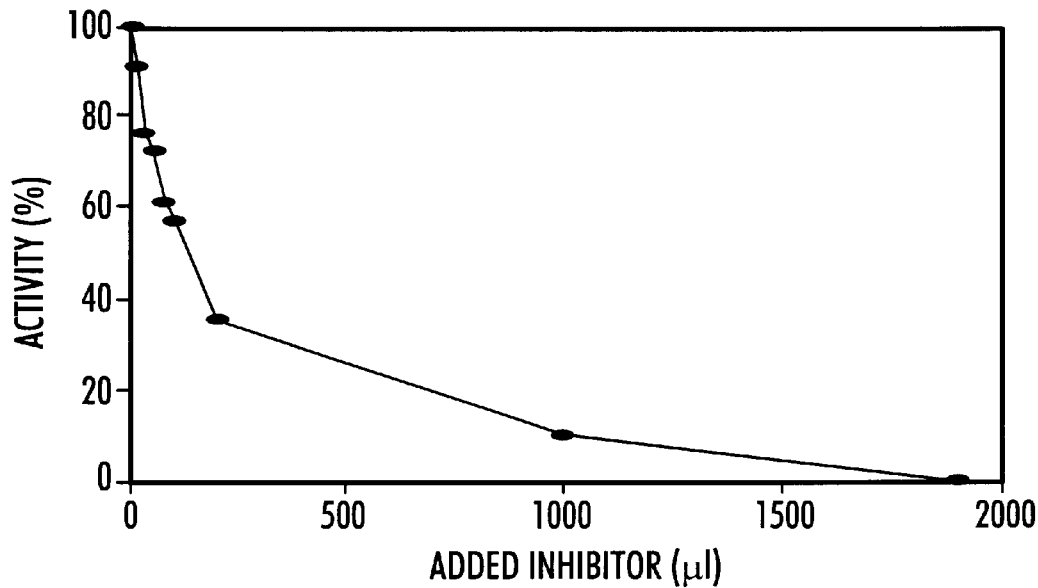
FIG. 7 shows inhibition of total invertase activity from injured sugar beets by means of invertase inhibitor derived from tobacco cell cultures.
Figure 8:
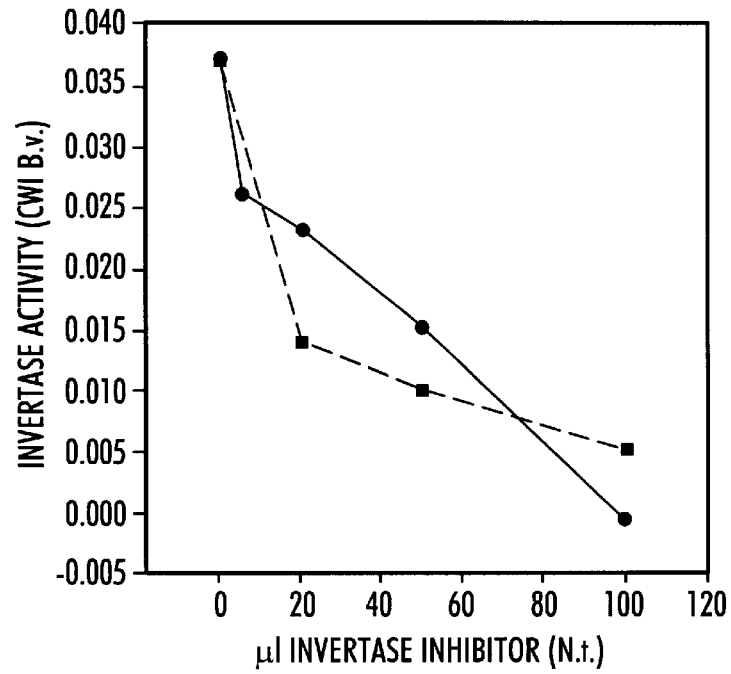
FIG. 8 shows inhibition of cell-wall invertase from sugar beet by means of the recombinant tobacco invertase inhibitor (see FIGS. 3–5). The circles show inhibition after preincubation of both proteins without sucrose; the squares show inhibition without preincubation.
Figure 9:
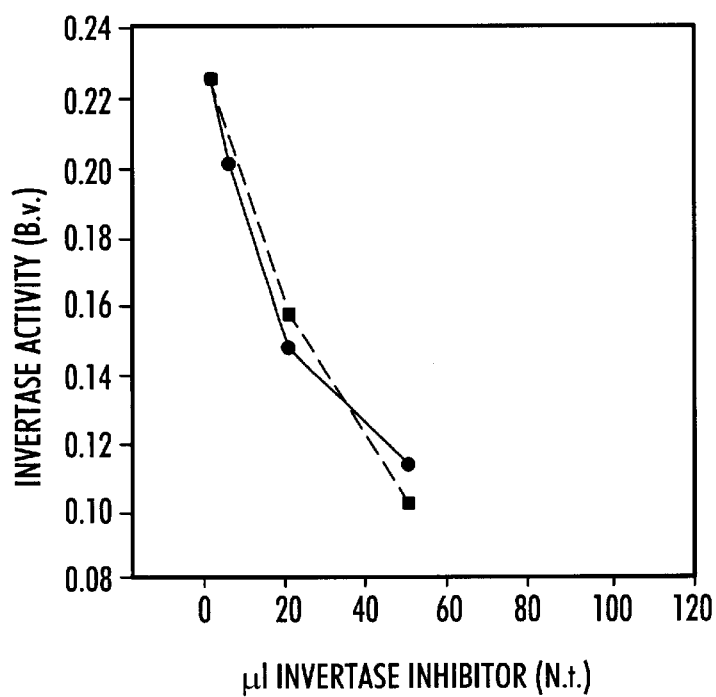
FIG. 9 shows inhibition of total invertase activity from injured sugar beets (vacuolar invertase+cell-wall invertase) by means of the recombinant tobacco invertase inhibitor (see FIGS. 3–5). The circles show inhibition after preincubation of both proteins without sucrose; the squares show inhibition without preincubation.

The invertase activity in injured sugar beets (FIG. 6) can be inhibited by the inhibitor protein isolated from tobacco cells (FIG. 7). Enzyme kinetics with recombinant tobacco inhibitor protein confirm that both the total invertase activity (FIG. 9) in injured sugar beets and the partially purified cell-wall invertase of sugar beet (FIG. 8) can be inhibited by the invertase inhibitor from tobacco.

Figure 10:
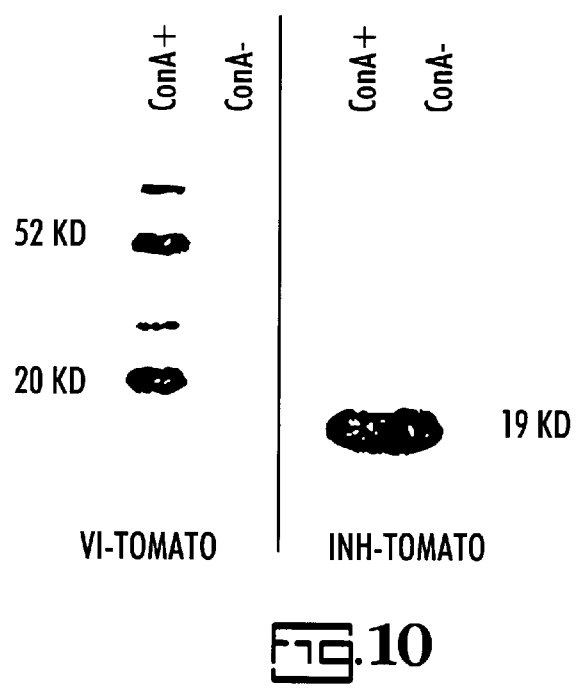
FIG. 10 shows the immunological identification of vacuolar invertase (VI) from tomato fruits, as well as the detection of a tomato inhibitor (INH) homologous to the tobacco invertase inhibitor. Both proteins were detected with polyclonal, monospecific antisera. After SDS-PAGE and Western Blot, the VI shows two cleavage products of 52 and 20 kDa. The VI binds completely to concanavalin A sepharose, whereas the tomato invertase inhibitor is present in roughly equal quantities of con A-binding and con A-nonbinding fractions.
Figure 11:
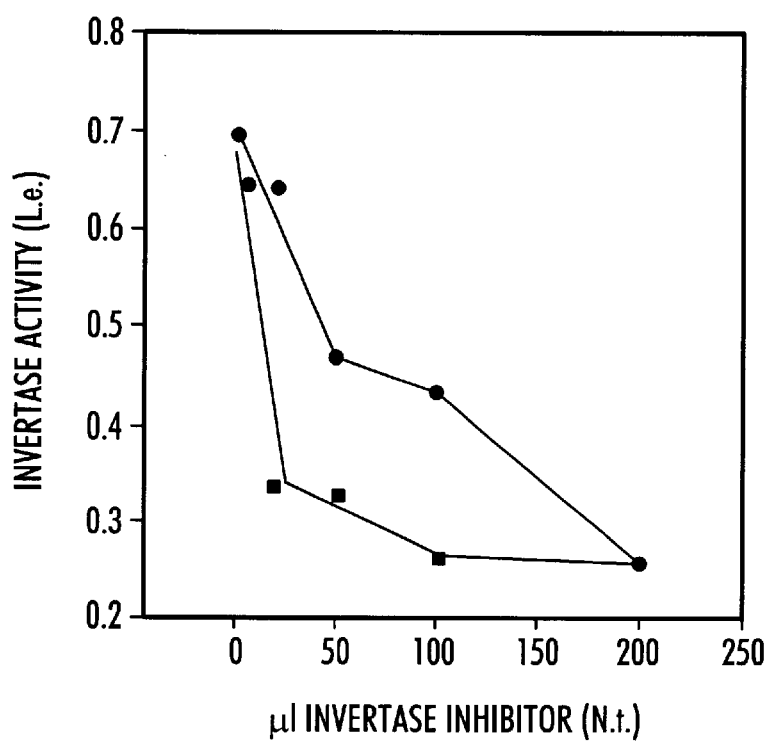
FIG. 11 shows inhibition of the tomato VI by means of the recombinant tobacco invertase inhibitor (see FIGS. 3–5). The circles show inhibition after preincubation of both proteins without sucrose; the squares show inhibition without preincubation.

In tomato fruits, vacuolar invertase is primarily expressed, which is degraded into two cleavage products (52 and 20 kDa, see FIG. 10) upon SDS-PAGE separation. Along with the vacuolar invertase, an invertase inhibitor of approximately 19 kDa, presumably localized in the cell-wall space, is also expressed; it cross-reacts with the antiserum against the tobacco invertase inhibitor (FIG. 10). The vacuolar invertase isolated from tomato fruits is likewise inhibited by the recombinant tobacco invertase inhibitor (FIG. 11). The striking sequence homology of a tomato cDNA partial sequence obtained by RT-PCR with the sequence of the tobacco invertase inhibitor (FIGS. 12 and 13) suggests that the tomato invertase inhibitor expressed in fruits might be compartmentalized (in the cell-wall space) with respect to the vacuolar invertase and thus does not inhibit the vacuolar invertase in vivo.

In summary, the apoplastic tobacco invertase inhibitor (FIG. 3) has been demonstrated to be capable of completely inhibiting both cell-wall invertases and vacuolar invertases, in particular of sugar beet and tomato. Given correct cellular targeting, the tobacco invertase inhibitor can thus be used in transgenic plants (sugar beet, potato, tomato) to reduce vacuolar invertases and/or invertases localized in the cell wall. The invertase inhibitor localized in the cytosol (FIGS. 14(a)–14(b)) regulates cytosolic invertases. Their inhibition in transgenic plants can also have an advantageous effect on the sucrose/hexose ratio.

What is claimed is:

1. An isolated nucleic acid comprising at least one nucleic acid sequence coding for a polypeptide capable of reducing the enzymatic activity of an invertase, said nucleic acid sequence selected from the group consisting of SEQ ID NO: 2; SEQ ID NO: 3; and SEQ ID NO: 4.

2. The nucleic acid according to claim 1, wherein said invertase is localized in a plant cell.

3. The nucleic acid according to claim 2, wherein said invertase is further localized in a plant cell at a site selected from the group consisting of a vacuole of said plant cell, a wall of said plant cell, and the cytosol of said plant cell.

4. The nucleic acid according to claim 1, wherein said invertase is selected from the group consisting of sugar beet, potato, and tomato invertases.

5. The nucleic acid according to claim 1, further comprising at least one nucleic acid sequence coding for a signal peptide.

6. The nucleic acid according to claim 5, wherein said signal peptide is an invertase signal peptide.

7. The nucleic acid according to claim 5, wherein said signal peptide is isolated from cell-wall invertase from tobacco.

8. The nucleic acid according to claim 1, further comprising at least one nucleic acid sequence coding for an endoplasmic reticulum retention sequence.

9. The nucleic acid according to claim 1, further comprising at least one nucleic acid sequence, said sequence comprising a promoter suitable for expression in plants.

10. The nucleic acid according to claim 9, wherein said promoter and said invertase are isolated from the same plant species.

11. The nucleic acid according to claim 9, wherein said promoter is specific to a plant selected from the group consisting of potato, tomato, and sugar beet.

12. A nucleic acid comprising:
   (a) a first nucleic acid sequence, called an inhibitor sequence, coding for a polypeptide inhibiting the enzymatic activity of an invertase, said sequence comprising a sequence selected from the group consisting of SEQ ID NO: 2; SEQ ID NO: 3; and SEQ ID NO: 4;
   (b) a second nucleic acid sequence, called a targeting sequence, coding for a targeting sequence;
   (c) a third nucleic acid sequence, called a signal sequence, coding for a signal peptide; and (d) a fourth nucleic acid sequence, called a promoter sequence, comprising a promoter sequence controlling expression of each of said nucleic acid sequences;

wherein said first, second, third, and fourth nucleic acid sequences are operatively linked in the order promoter sequence, signal sequence, inhibitor sequence, and targeting sequence such that expression of said sequences provides a polypeptide capable of inhibiting the enzymatic activity of an invertase.

13. A nucleic acid vector comprising a nucleic acid sequence according to claim 1, said nucleic acid sequence being operatively linked to an expression control sequence.

14. The nucleic acid vector according to claim 13, wherein said vector is a plasmid selected from the group consisting of the Ti plasmid of *Agrobacterium tumefaciens,* a binary plasmid system of *Agrobacterium tumefaciens,* and the Ri plasmid of *Agrobacterium rhizogenes.*

15. A host cell which is a recombinant cell that has been transformed with a recombinant nucleic acid, said recombinant nucleic acid having at least one nucleic acid sequence according to claim 1.

16. A transgenic plant comprising at least one recombinant nucleic acid, said recombinant nucleic acid comprising at least one nucleic acid according to claim 1.

17. The transgenic plant according to claim 16, wherein said plant is isolated from a wild type plant selected from the group consisting of plants having starchy tubers, plants having starchy roots, potatoes, sweet potatoes, cassava, sugar plants, tomato, and maize.

18. A method of producing a transgenic plant from a wild type plant, said method comprising the steps:

(a) isolating a nucleic acid, said nucleic acid comprising a nucleic acid sequence coding for a peptide that inhibits the enzymatic activity of an invertase, said nucleic acid selected from the group consisting of SEQ ID NO:2; SEQ ID NO:3; and SEQ ID NO:4;

(b) transforming a plant cell of said wild type plant by stably integrating said nucleic acid into the genome of said plant cell; and (c) regenerating said plant cell to produce a transgenic plant.

19. The method according to claim 18, wherein said wild type plant is selected from the group consisting of sugar beet, potato, tomato, and sugar cane.

20. The transgenic plant according to claim 17, wherein said sugar plants are sugar cane or sugar beets.

21. An isolated nucleic acid sequence comprising a nucleic acid sequence coding for a polypeptide that reduces the enzymatic activity of an invertase, said nucleic acid sequence selected from the group consisting of (a) SEQ ID NO. 2;

(b) SEQ ID NO. 3;

(c) SEQ ID NO. 4; and (d) nucleic acid sequences encoding polypeptides, said polypeptides having at least 70% sequence identity to a sequence selected from the group consisting of SEQ ID NO. 6; SEQ ID NO. 7; and SEQ ID NO. 8;

wherein said nucleic acid sequence, when introduced into an expression vector and expressed in *E. coli,* produces a polypeptide capable of inhibiting the enzymatic activity of an invertase.

22. An isolated nucleic acid comprising a nucleic acid sequence coding for a polypeptide that reduces the enzymatic activity of an invertase, said polypeptide having at least 70% sequence identity to a sequence selected from the group consisting of SEQ ID NO. 6; SEQ ID NO. 7; and SEQ ID NO. 8; wherein said nucleic acid sequence, when introduced into an expression vector and expressed in *E. coli,* produces said polypeptide capable of inhibiting the enzymatic activity of an invertase.

* * * * *

SEQUENCE LISTING

<160> NUMBER OF SEQ ID NOS: 9

<210> SEQ ID NO 1
<211> LENGTH: 1701
<212> TYPE: DNA
<213> ORGANISM: Nicotiana tabacum
<220> FEATURE:
<221> NAME/KEY: unsure
<222> LOCATION: (1232)..(1243)
<223> OTHER INFORMATION: Unsurance concerning the identity of
      nucleotides 1232, 1240 and 1243.

<400> SEQUENCE: 1

```
atgggcgagg aaaatgtcgt gcaggtgata actcagaaca caccgaatta t caagctgct      60 ggaaagatgc ttgaagagaa aagaaggaat ttattttgga ctccttgtgc t gcatattgt     120 attgatcgca tccttgaaga ctttgtgaaa ataaaatggg tcagagaatg c atggaaaaa     180 gcccaaaaaa tcaccaagtt catttacaat agtttctggt tgttaagtct c atgaaaaaa     240 gaatttacag ctggacagga actcttgaaa ccctctttta ctcgatattc t tcaaccttc     300 gctactgttc agagcttgtt ggaccacaga aatggtctta agaggatgtt c cagtcaaat     360 aaatggcttt cgtcccggta ttcaaagctg gaagatggta aagaggtgga g aaaattgta     420 ctaaatgcca ccttctggag gaaaatgcag tatgttagga aatcagtgga c ccattttag     480 aagtgcttca aaaatcaat agcaacgaaa gccattaata cccttcattt a caacaatgt     540 ataccaggca aaacttgctg tcaaaaccaa tcataatgac gacggggcaa a tatcggaac     600 attttggata tcatagacag ccactggaat tcattatctc atcatcctct c tatctagca     660 gcacactttc tgaatccatc ataccggtat cgtcctgatt ttgttccgca t ccagaggtt     720 gtacgaggac tgaatgcatg cattgtgcga ttggagccaa acaatgcaag a agaatttct     780 gcatccatgc aaatatcaga tttcaactct gcttaaagct gattttggaa c agatttggc     840
```

-continued

```
acttagcacc agaacggagc ttaatcctgc tgcttggtgg caacaacatg g ataaattgt      900 tagagctcca ccgatagctg gacgaatact agcagactgt cacttggtgt g agcacaatt      960 ggagttatat catcagatcc acagtcagag gcacaaccgt gtagcacaga a agattaaac     1020 gatgtcacat acgtccacta taacctgaga cttagggatc gtcagataag g aaaatgcct     1080 atcatccaat tttcctcgat agtgttctgc aagaaatttg ctgtatgatt g gattgtaga     1140 gtcagagaaa ccagttttgc aagacgatga ggaaatgctt tatagtgaaa t ggaactggt     1200 gagtatgaga atgatttcat ggaccatgat gntggaaatn canacttaag g aagggatca     1260 ttggagatgg taactttagc tggtgaagca gaaccctag aagttaatcc t gacaatact      1320 ggtacagcta cagatgatga ttctgatctc aattttcttg ataatgagtt g agtgattag     1380 tgccttgaac cagaacccaa atgcacagca gttaacatgt ttggtaacca c tcaactact     1440 ggcaatgtat tctattatcg caagtccttt agctatctct cccaatcact t tcttggcaa     1500 aatgtgcact gccagttggg cgagtgggga cgggaaaggg gggaaaagtc g gaaagagcc     1560 tgtgtagaag ttagagatca gcattacagg agggcactgg agtgtacatg t caaagtact     1620 tcgtttctta acctctcact gttcatgttt agtcattgtt tgctcttatt c agttttcct     1680 tcaaaaaaaa aaaaaaaaa a                                                 1701

<210> SEQ ID NO 2
<211> LENGTH: 649
<212> TYPE: DNA
<213> ORGANISM: Nicotiana tabacum

<400> SEQUENCE: 2
agaaaatcta actttggttc tctctctctt gtcttttcca acttcaaaaa t gaagaattt       60 gattttccta acgatgtttc tgactatatt actacaaaca aacgccaata a tctagtaga      120 aactacatgc aaaacacac caaattacca actttgtctg aaaactctgc t ttcggacaa      180 acgaagtgca cagggggata tcacaacgtt ggcactaatt atggtcgatg c aataaaagc      240 taaagctaat caggctgcag tgacaatttc gaaactccgg cattcgaatc c ccctgcagc      300 ttggaaaggt cctttgaaaa actgtgcctt ttcatataag gtaatttaa c agcaagttt       360 gcctgaagca attgaagcat tgacaaaagg agatccaaaa tttgctgaag a tggaatggt      420 aggttcatct ggagatgcac aagaatgtga ggagtatttc aagggtagta a atcaccatt      480 ttctgcatta aatatagcag ttcatgaact ttctgatgtt gggagagcta t tgtcagaaa      540 tttattgtga tatatatgca ctactcttat acaagtgtaa caatattatc g atcagaaat      600 ttattatgat gtgcctgtgt attcacacgt gaaaaaaaaa aaaaaaaaa                   649

<210> SEQ ID NO 3
<211> LENGTH: 307
<212> TYPE: DNA
<213> ORGANISM: Lycopersicon esculentum

<400> SEQUENCE: 3
aagaacacac cgaattacca tttgtgtgtg aaaactttgt ctttagacaa a agaagtgaa       60 aaagcaggag atattacaac attagcatta attatggttg atgctattaa a tctaaagct      120 aatcaagctg ctaatactat ttcaaaactt aggcattcta atcctcctca a gcttggaaa      180 gatccttttga agaattgtgc cttttcgtat aaggtaattt taacagcaag t atgccagaa      240 gcaatagaag cattaacaaa aggtgatcca aaatttgcag aagatggaat g gtcggatca      300 tcaggtg                                                                 307
```

```
<210> SEQ ID NO 4
<211> LENGTH: 811
<212> TYPE: DNA
<213> ORGANISM: Nicotiana tabacum

<400> SEQUENCE: 4
cggcacgaga acaaaaccaa acacctttcc tttggcctct cctcctttta t cttttatat      60 caatcctcat cttcaataac accactctca aaacaaatga gaaacttatt c cccatattt     120 atgttaatca ccaatctagc attcaacgac aacaacaaca gtaataatat c atcaacacg     180 acctgcagag ccaccacaaa ctaccccttg tgcctcacca ccctccactc t gatccccgt     240 acctccgagg ccgaggggc ggacctcacc accctcggcc tcgtcatggt a gatgcggta     300 aaattaaagt ccatcgaaat aatgaaaagt ataaaaaaac tcgaaaaatc g aaccccgag     360 ttgagactac ctcttagcca atgttacata gtgtattatg ctgttctaca t gctgatgta     420 actgttgctg ttgaagcttt aaaagagga gtccctaaat ttgctgaaaa t ggaatggtt     480 gatgttgctg tagaagcaga aacttgtgag tttagtttta agtataatgg a ttggtttct     540 ccagtttctg atatgaataa ggagattatt gaactgtctt ctgtggctaa a tctattatt     600 agaatgctat tatgaggaaa ttaaagaacc aaagatacaa ggttctggtt a tgttagttt     660 attagtgctg taataggatt tttatattcc tgtgtttttt ttgctttttt t atttcattt     720 gggtgcttgt gtgtatatgt gaaatgagt gtgaattatg tcaaacataa a catagatta     780 gaaattactc ctgaaaaaaa aaaaaaaaa a                                      811

<210> SEQ ID NO 5
<211> LENGTH: 159
<212> TYPE: PRT
<213> ORGANISM: Nicotiana tabacum

<400> SEQUENCE: 5

Met Gly Glu Glu Asn Val Val Gln Val Ile Thr Gln Asn Thr Pro Asn
 1               5                  10                  15

Tyr Gln Ala Ala Gly Lys Met Leu Glu Glu Lys Arg Arg Asn Leu Phe
                20                  25                  30

Trp Thr Pro Cys Ala Ala Tyr Cys Ile Asp Arg Ile Leu Glu Asp Phe
            35                  40                  45

Val Lys Ile Lys Trp Val Arg Glu Cys Met Glu Lys Ala Gln Lys Ile
        50                  55                  60

Thr Lys Phe Ile Tyr Asn Ser Phe Trp Leu Ser Leu Met Lys Lys
 65                 70                  75                  80

Glu Phe Thr Ala Gly Gln Glu Leu Leu Lys Pro Ser Phe Thr Arg Tyr
                85                  90                  95

Ser Ser Thr Phe Ala Thr Val Gln Ser Leu Leu Asp His Arg Asn Gly
            100                 105                 110

Leu Lys Arg Met Phe Gln Ser Asn Lys Trp Leu Ser Ser Arg Tyr Ser
        115                 120                 125

Lys Leu Glu Asp Gly Lys Glu Val Glu Lys Ile Val Leu Asn Ala Thr
    130                 135                 140

Phe Trp Arg Lys Met Gln Tyr Val Arg Lys Ser Val Asp Pro Phe
145                 150                 155

<210> SEQ ID NO 6
<211> LENGTH: 182
<212> TYPE: PRT
```

```
<213> ORGANISM: Nicotiana tabacum

<400> SEQUENCE: 6

Glu Asn Leu Thr Leu Val Leu Ser Leu Ser Phe Pro Thr Ser Lys
 1               5                  10                  15

Met Lys Asn Leu Ile Phe Leu Thr Met Phe Leu Thr Ile Leu Leu Gln
                20                  25                  30

Thr Asn Ala Asn Asn Leu Val Glu Thr Thr Cys Lys Asn Thr Pro Asn
            35                  40                  45

Tyr Gln Leu Cys Leu Lys Thr Leu Leu Ser Asp Lys Arg Ser Ala Thr
        50                  55                  60

Gly Asp Ile Thr Thr Leu Ala Leu Ile Met Val Asp Ala Ile Lys Ala
 65                  70                  75                  80

Lys Ala Asn Gln Ala Ala Val Thr Ile Ser Lys Leu Arg His Ser Asn
                85                  90                  95

Pro Pro Ala Ala Trp Lys Gly Pro Leu Lys Asn Cys Ala Phe Ser Tyr
            100                 105                 110

Lys Val Ile Leu Thr Ala Ser Leu Pro Glu Ala Ile Glu Ala Leu Thr
        115                 120                 125

Lys Gly Asp Pro Lys Phe Ala Glu Asp Gly Met Val Gly Ser Ser Gly
        130                 135                 140

Asp Ala Gln Glu Cys Glu Glu Tyr Phe Lys Gly Ser Lys Ser Pro Phe
145                 150                 155                 160

Ser Ala Leu Asn Ile Ala Val His Glu Leu Ser Asp Val Gly Arg Ala
                165                 170                 175

Ile Val Arg Asn Leu Leu
            180

<210> SEQ ID NO 7
<211> LENGTH: 102
<212> TYPE: PRT
<213> ORGANISM: Lycopersicon esculentum

<400> SEQUENCE: 7

Lys Asn Thr Pro Asn Tyr His Leu Cys Val Lys Thr Leu Ser Leu Asp
 1               5                  10                  15

Lys Arg Ser Glu Lys Ala Gly Asp Ile Thr Thr Leu Ala Leu Ile Met
                20                  25                  30

Val Asp Ala Ile Lys Ser Lys Ala Asn Gln Ala Ala Asn Thr Ile Ser
            35                  40                  45

Lys Leu Arg His Ser Asn Pro Pro Gln Ala Trp Lys Asp Pro Leu Lys
        50                  55                  60

Asn Cys Ala Phe Ser Tyr Lys Val Ile Leu Thr Ala Ser Met Pro Glu
 65                  70                  75                  80

Ala Ile Glu Ala Leu Thr Lys Gly Asp Pro Lys Phe Ala Glu Asp Gly
                85                  90                  95

Met Val Gly Ser Ser Gly
            100

<210> SEQ ID NO 8
<211> LENGTH: 204
<212> TYPE: PRT
<213> ORGANISM: Nicotiana tabacum

<400> SEQUENCE: 8

Arg His Glu Asn Lys Thr Lys His Leu Ser Phe Gly Leu Ser Ser Phe
 1               5                  10                  15
```

-continued

```
Tyr Leu Leu Tyr Gln Ser Ser Ser Ile Thr Pro Leu Ser Lys Gln
            20              25              30

Met Arg Asn Leu Phe Pro Ile Phe Met Leu Ile Thr Asn Leu Ala Phe
            35              40              45

Asn Asp Asn Asn Asn Ser Asn Asn Ile Ile Asn Thr Thr Cys Arg Ala
            50              55              60

Thr Thr Asn Tyr Pro Leu Cys Leu Thr Thr Leu His Ser Asp Pro Arg
65              70              75              80

Thr Ser Glu Ala Glu Gly Ala Asp Leu Thr Thr Leu Gly Leu Val Met
            85              90              95

Val Asp Ala Val Lys Leu Lys Ser Ile Glu Ile Met Lys Ser Ile Lys
            100             105             110

Lys Leu Glu Lys Ser Asn Pro Glu Leu Arg Leu Pro Leu Ser Gln Cys
            115             120             125

Tyr Ile Val Tyr Tyr Ala Val Leu His Ala Asp Val Thr Val Ala Val
            130             135             140

Glu Ala Leu Lys Arg Gly Val Pro Lys Phe Ala Glu Asn Gly Met Val
145             150             155             160

Asp Val Ala Val Glu Ala Glu Thr Cys Glu Phe Ser Phe Lys Tyr Asn
            165             170             175

Gly Leu Val Ser Pro Val Ser Asp Met Asn Lys Glu Ile Ile Glu Leu
            180             185             190

Ser Ser Val Ala Lys Ser Ile Ile Arg Met Leu Leu
            195             200

<210> SEQ ID NO 9
<211> LENGTH: 18
<212> TYPE: PRT
<213> ORGANISM: Hordeum sp.

<400> SEQUENCE: 9

Leu Glu Gly Val Phe Ala Glu Ile Ala Ala Ser Asn Ser Thr Leu Val
1               5               10              15

Ala Glu
```